United States Patent [19]

Grady

[11] 4,426,725

[45] Jan. 17, 1984

[54] BIPLANAR VARIABLE ANGLE X-RAY EXAMINING APPARATUS

[76] Inventor: John K. Grady, 111 Slough Rd., Harvard, Mass. 01451

[21] Appl. No.: 376,109

[22] Filed: May 7, 1982

Related U.S. Application Data

[63] Continuation-in-part of Ser. No. 67,605, Aug. 20, 1979, abandoned, and a continuation-in-part of Ser. No. 148,298, May 9, 1980, abandoned.

[51] Int. Cl.³ .............................................. A61B 6/00
[52] U.S. Cl. ...................................... 378/196; 378/62
[58] Field of Search .............. 378/196, 190, 179, 197, 378/174, 181, 41, 42, 62, 9, 6, 87, 89

[56] References Cited

U.S. PATENT DOCUMENTS 3,809,904  5/1974  Clarke et al. ..................... 378/89

Primary Examiner—Alfred E. Smith
Assistant Examiner—T. N. Grigsby
Attorney, Agent, or Firm—James H. Grover

[57] ABSTRACT

X-ray apparatus is shown in which there are two radiological sets, each set including an X-ray tube and radiation receptor (e.g., film holder or image intensifier) and means supporting them on a common radiation axis. The two radiation axes of the respective radiological sets intersect at an isocenter at which the subject of examination, e.g., the human heart, may be located; and at least one set is rotatable on a rotation axis through the isocenter and perpendicular to the radiation axes independently of, and relative to, the radiation axis of the other set. One or both of the sets may be retracted from alignment with the isocenter without disturbing the patient to allow unobstructed access and both sets may be independently rotatable.

23 Claims, 15 Drawing Figures

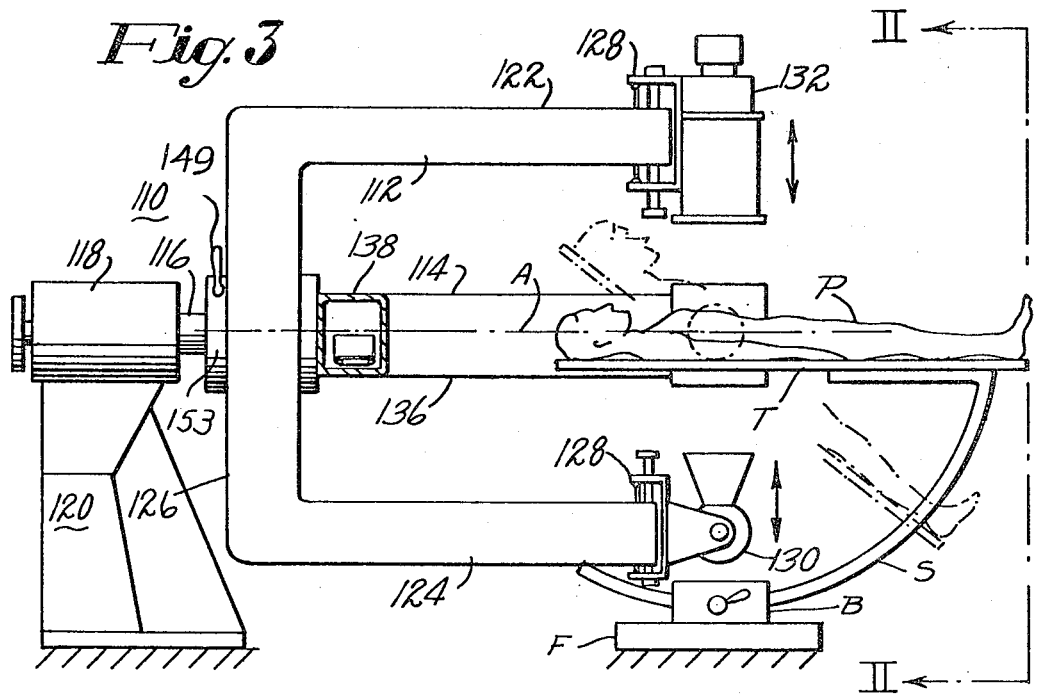
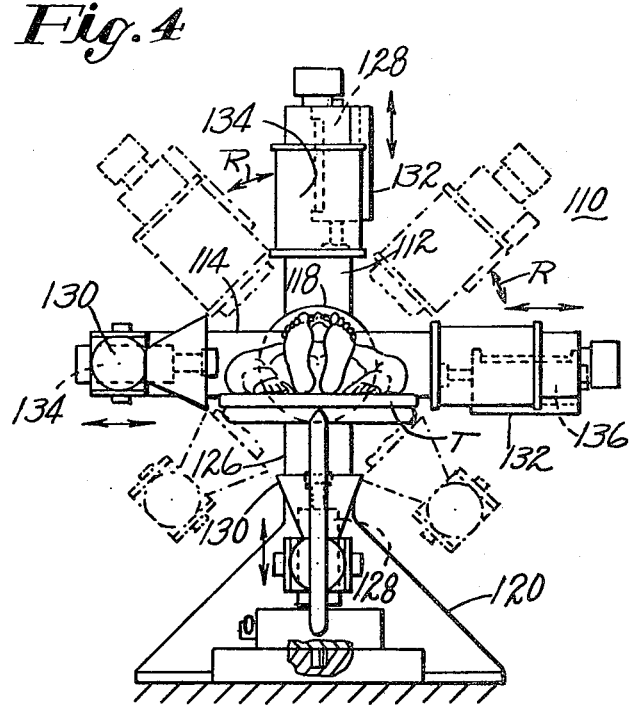

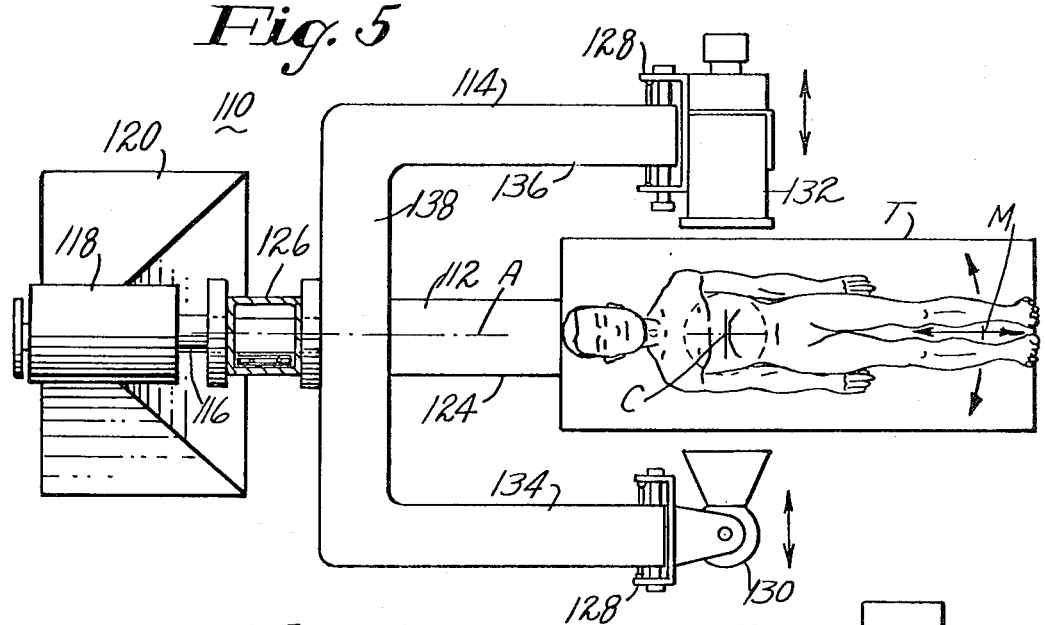
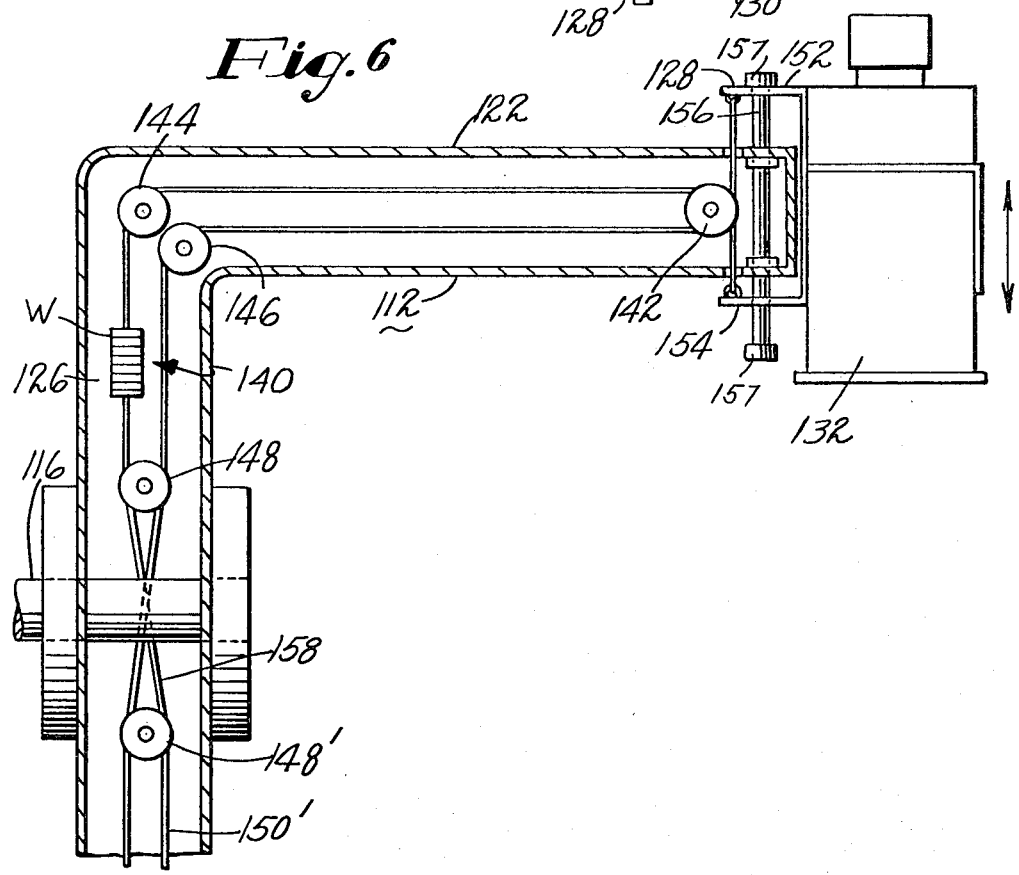

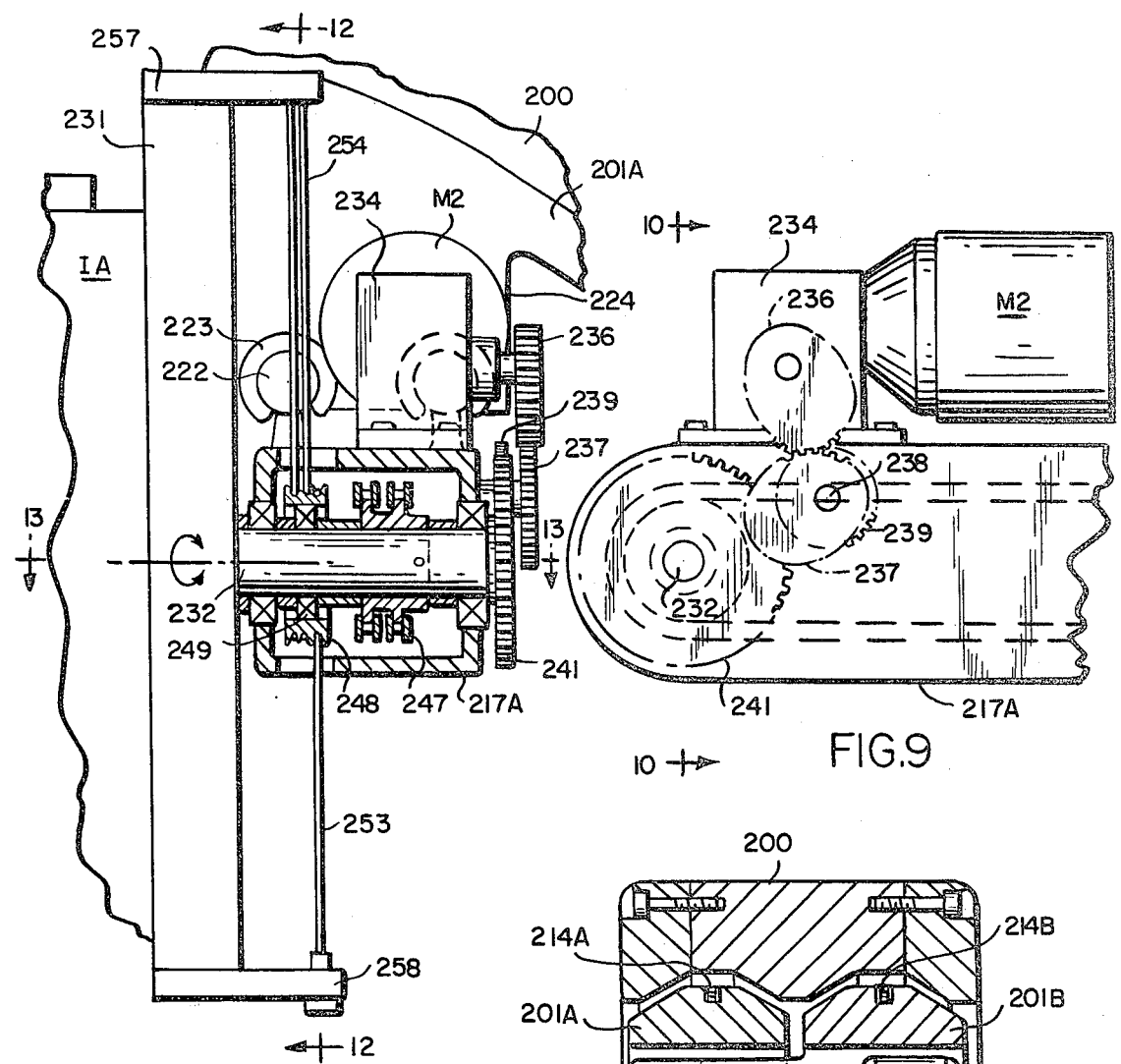
FIG.10
FIG.9
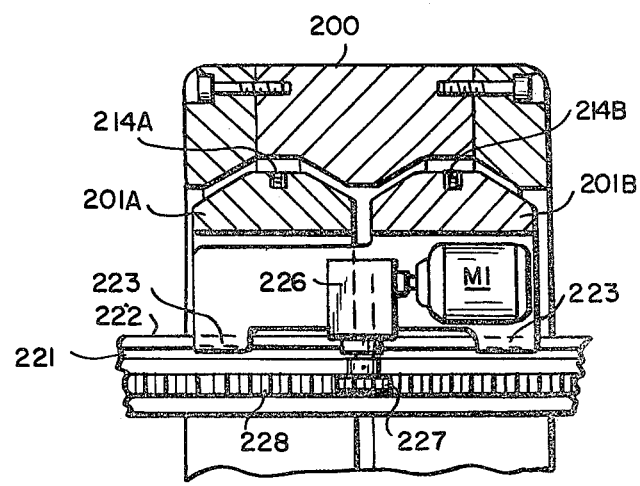
FIG.11
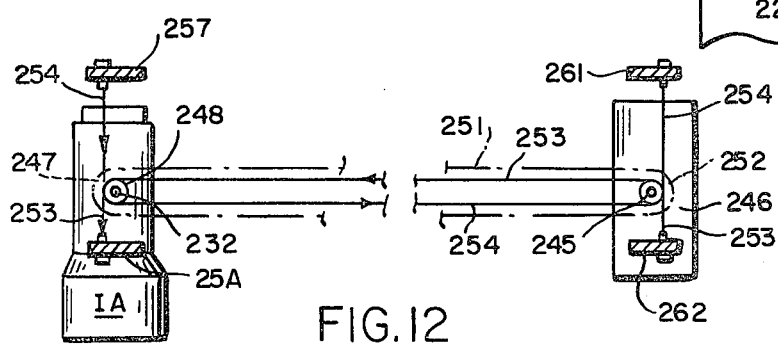
FIG.12

BIPLANAR VARIABLE ANGLE X-RAY EXAMINING APPARATUS

This application is a continuation in part of pending applications of John K. Grady, Ser. No. 67,605, filed Aug. 20, 1979 and now abandoned, entitled RADIOLOGICAL X-RAY SYSTEM, and Ser. No. 148,298, filed May 9, 1980 and now abandoned, entitled RADIOLOGICAL SUPPORT APPARATUS.

BACKGROUND OF THE INVENTION

Some X-ray examining procedures can involve more than routine discomfort and hazards to a diagnostic patient. In patients with coronary artery disease, oblique views of the right and left anterior ventricle are considered optimal for assessment of regional wall motion. With equipment previously used, the patient was strapped to a cradle and a radiological examination on one plane was made and then the patient was tilted on the cradle to provide for examination in the second plane. Such examinations are not desirable because the procedure of tilting the patient to take biplanar views can be traumatic. In addition to the patient's motional discomfort, the time required for a series of biplanar X-ray exposures through the organ examined and the accumulation of X-ray dosage should be minimized. Also the amount of radiopaque or radioisotopic injected material must be minimized while maximizing the number of exposures over a wide range of angles. For example, in radiological examination of the heart a radiopaque liquid, toxic in large concentrations, is injected through a suitable arterial system for each X-ray exposure which must be made quickly. The injection toxicity, discomfort, and elapsed time can be reduced by one half by making two X-ray exposures simultaneously or in rapid sequence in two planes through the subject. Apparatus for taking two biplanar X-ray exposures of a subject is shown in U.S. Pat. No. 3,459,885 to Andersson and U.S. Pat. No. 3,659,099 to Bertheau. While the apparatus of these patents simultaneous biplanar exposures of a subject at the intersection of the two axes, the two axes are fixed at a right angle to each other. Two biplanar exposures at right angles through a subject are not always at the best or the necessary angle for useful examination of the subject. If the optimum angle or plane for one exposure is selected, the relatively fixed angle of the second exposure may be useless. Moreover, it is often desirable to repeat the exposure in one plane while changing the second exposure plane. Accordingly, one object of the present invention is to provide apparatus for biplanar radiological examination on two axes through a common subject which permits adjustment of one axis relative to the other.

Also, although it is possible to make fixed angle biplanar exposures with the apparatus of the Andersson and Bertheau patents, both patentees recognize the problem of ready access to the patient through the two sets of X-ray equipment. It is a further object of the present invention to permit free access to the patient in biplane X-ray apparatus.

SUMMARY OF THE INVENTION

According to the invention, radiological apparatus for examination of a subject comprises a first radiological examining set including first radiation source means, first radiation receptor means and first support means for holding the first source and receptor means on a first radiation axis; and a second radiological examining set including second radiation source means, second radiation receptor means and second support means for holding the second source and receptor means on a second radiation axis aligned to intersect the first radiation axis at an isocenter, the first support means being rotational independently of the second support means about an axis intersecting the isocenter; whereby a series of substantially simultaneous radiological examinations can be made on both radiation axes through the subject at variable angles between the radiation axes.

Further, according to the invention, the support means for one radiation source or receptor means in a set is movable independently of the support means for the other radiation means in the same set and includes means guiding the independent movement of the support means on a path from a position of the radiation means in alignment with the isocenter to a position remote from the isocenter and freeing access to a subject at the isocenter.

DRAWINGS

FIG. 3 is a side elevation of another form of radiological examining apparatus, partly broken away, as shown in application Ser. No. 148,298 now abandoned;

FIG. 4 is an end view from lines II—II of FIG. 3;

FIG. 5 is a plan view of the apparatus of FIG. 3, partly broken away, and including a patient support table;

FIG. 6 is an enlarged, sectional view of a portion of FIG. 5;

FIG. 9 is a section, enlarged on line 9—9 of FIG. 7;

FIG. 10 is a section on line 10—10 of FIG. 9;

FIG. 11 is an enlarged section on line 11—11 of FIG. 7;

FIG. 12 is a schematic drawing of a counterweighting cable system on line 12—12 of FIG. 10;

DESCRIPTION

Figure 1:
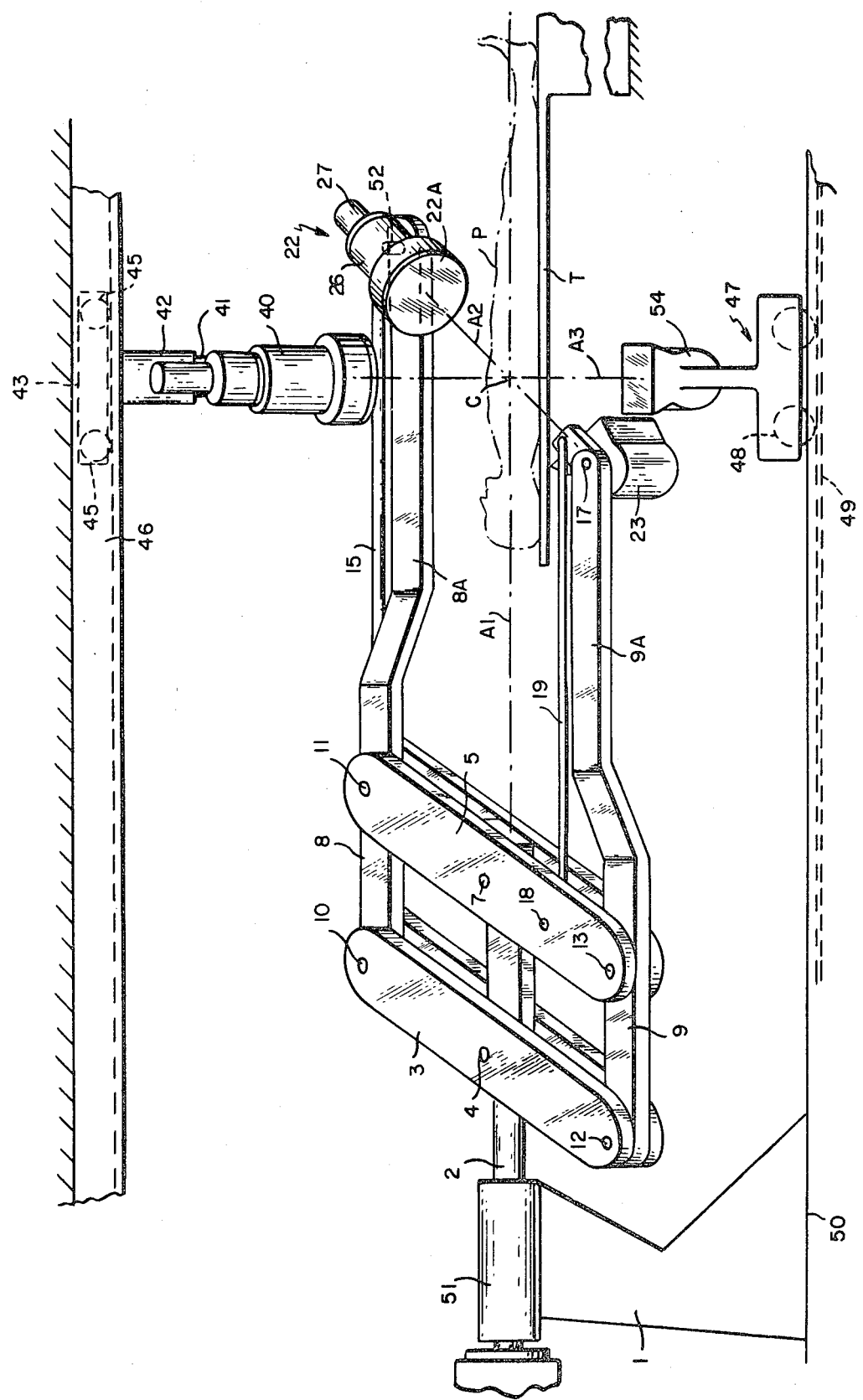
FIG. 1 is a side elevation of one form of radiological examining apparatus as shown in application Ser. No. 67,605 now abandoned.
Figure 2:
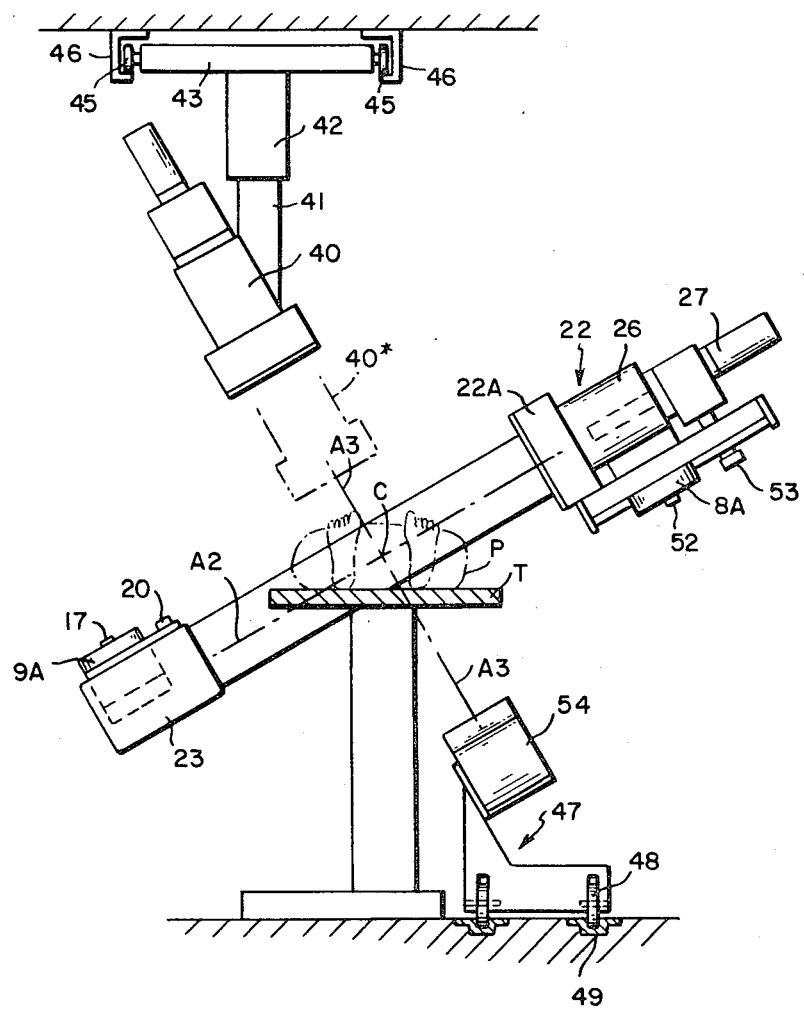
FIG. 2 is an end view of the apparatus of FIG. 1.
Figure 7:
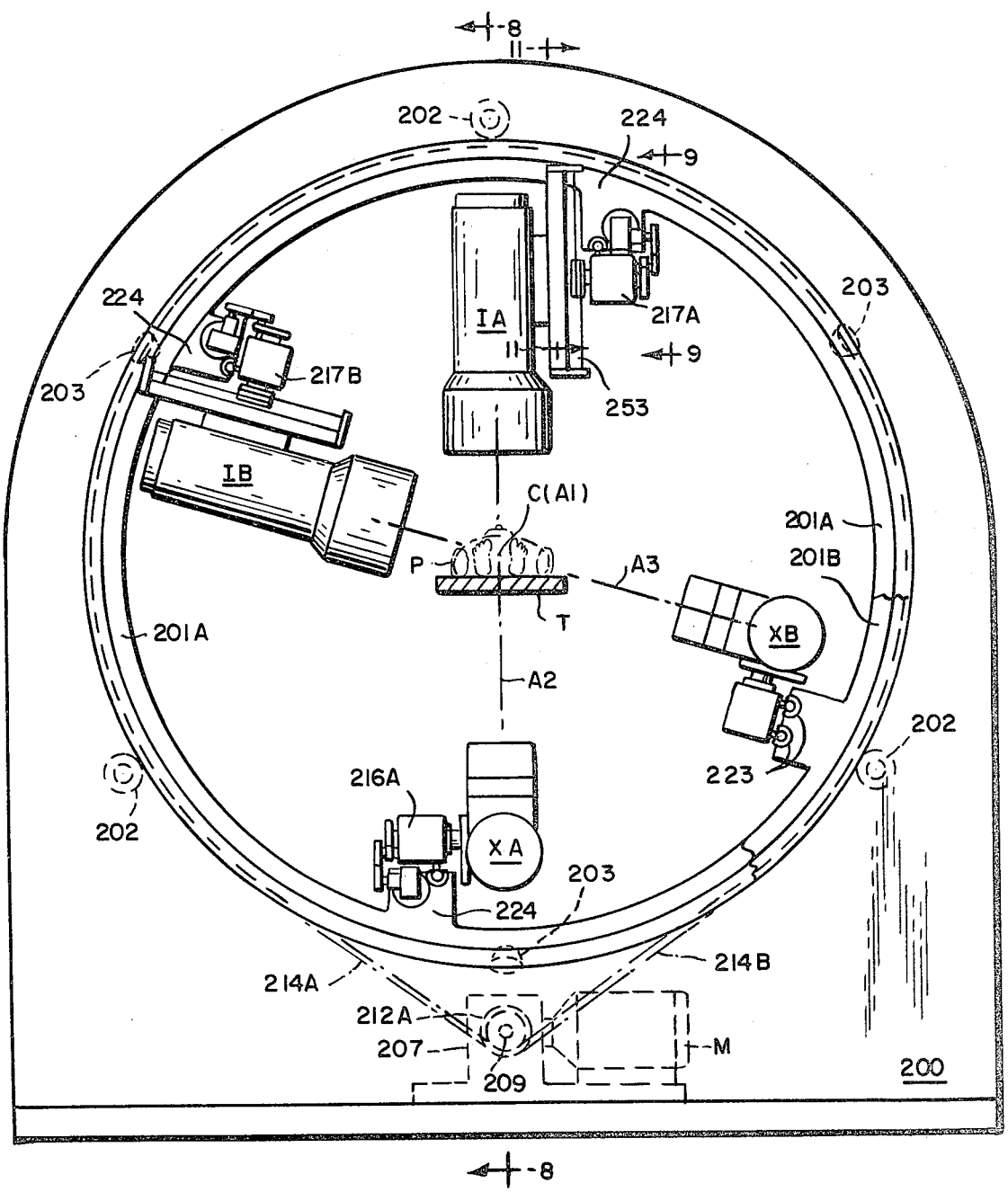
FIG. 7 is an end elevation of a further form of radiological examining apparatus.

I—The Embodiment of FIGS. 1 and 2
II—The Embodiment of FIGS. 3 to 6
III—The Embodiment of FIGS. 7 to 15

I—The Embodiment of FIGS. 1 and 2

As shown in FIGS. 1 and 2, a patient P is disposed in a fixed position on a radiation-transparent table T. The patient is shown with his heart located at an isocenter C which is the intersection of an axis of rotation A1 of the radiological examining system and a common radiation axis A2 between an X-ray tube 23 and a radiation image intensifier 22 and a common radiation axis A3 between an X-ray tube 54 and a radiation image intensifier 40. When filming the ventricle of the heart located at isocenter C, the axis A3 can be perpendicular to axis A2 which, in turn, can be perpendicular to axis A1. When providing cardiac angiography, the heart can be examined by tilting the X-ray tube 23 through 360° of angle around central axis A1 of the system which is aligned with the long axis of the patient. The common axis A2 can also be rotated 90° about a secondary axis perpendicular to the central axis A2 about the isocenter C, that is a solid angle defined from the head to the foot. Simultaneously, the radiological apparatus 40, 41 is focused upon the isocenter C thereby allowing oblique biplane filming of the same point.

The system for providing these types of X-rays comprises a heavy base 1 anchored to the floor 50 of the examining room, the base 1 having a central rotor shaft 2 journaled in rotor bearing 51. A first transverse member 3 extending at a right angle to the rotor shaft 2 is pivotally attached to the rotor shaft at 4. A second transverse member 5 parallel to the first transverse member 3 is pivotally supported at the distal end of the rotor shaft 2 at 7. Upper and lower support arms 8 and 9 are pivotally connected by bearing pins 10, 11, 12 and 13 to form an angularly adjustable parallelogram (3, 5, 8, 9) whose sides are of a fixed length between the pivotal connections, that is the distance between pin 10 and 12 is the same as the distance between pins 11 and 13 and the distance between pins 10 and 11 is the same as the distance between 12 and 13. Upper and lower support arms 8 and 9 have extensions 8A and 9A from the parallelogram for a distance sufficient to allow the table T and the patient P to be located close to the transverse member 5. At the distal ends of the extensions 8A and 9A are two pivots 52 and 17 for the image intensifier 22 and the X-ray tube 23. The pivot points 12, 13 and 17 are in a straight line parallel to the central axis A1 and spaced the same distance from the central axis as a line through pivot points 10, 11 and 52. One end of a first link 15 is pivotally attached to the second transverse member 5 and the other end is pivotally attached to the image intensifier 22 at 53. Similarly one end of a second link 19 is pivotally attached to a pivot point 18 in a second transverse member 5 and pivot point 20 of X-ray tube 23. The distances between points 17 and 20 and points 52 and 53 are equal, as are the distances between points 18 and 13 and point 11 and the unshown point attaching link 15 to second transverse member 5. In this way movement of the first transverse member 3 around point 4 will cause X-ray tube 23 and image intensifier 22 to move simultaneously in equal angles respectively around points 17 and 52. Simultaneously, equal angular movement of X-ray tube 23 and image intensifier 22 maintains these two units on a common axis, as the equipment is angulated over the long axis A1 of the patient around the isocenter C.

The image intensifier 22 includes a fluorescent imaging plate 22A which stimulates image intensifier stages to produce an optical image of required brightness. The intensifier image enters a beam splitting image distributor 26 of known design and transmits the image to an image recorder 27, such as a television camera. The camera 27, the image distributor 26 and the intensifier 22A are on a common axis which is coincident with the radiation axis A2.

According to the present invention, we have found that for certain angiographic examinations we can move the X-ray tube 23 and the image intensifier 22 through loci which can define a spheroidal shape around the isocenter C while simultaneously focusing upon the same isocenter from a different angle. Such examinations are particularly valuable in estimating the ventricular volumes. This oblique biplanar examination is provided, without moving the patient, by including a second radiological examining apparatus in the radiological examining system. The apparatus includes an X-ray tube 54 and an image intensifier 40. The image intensifier and the X-ray tube are constructed in a manner similar to equipment used in the radiological examining device described previously.

The radiological intensifier 40 is affixed to a support piston 41 that is slidably held by a cylinder 42. The support piston 41 is positioned perpendicular to the central axis A1 and can be raised or lowered through counter weights (not shown) so as to place the intensifier 40 on the common axis A3 with X-ray tube 54. X-ray intensifier 40 is also slidably retained on support piston 41 so that it can be reciprocated along common axis A3 to vary the focus (as shown in position 40*) and provide enlargements of the area of the organ being X-rayed. The cylinder 42 is attached to a carrier 43 that has wheels 45 mounted within channels 46, each of which is preferably disposed parallel to central axis 46. X-ray tube 54 is disposed upon a table and stand 47 that is supported by wheels 48 which travel in tracks 49, each of which is parallel to the central axis A1. In use, the units of the radiological examining apparatus are moved on the two sets of tracks 46 and 49 so that the common axis A3 falls into alignment with the isocenter C. Preferably, stops are disposed on the tracks 46 and 49 so that the apparatus can be easily wheeled by the transverse members 3 and 5 to enable the technicians to work upon the patient.

In summary, the apparatus of FIGS. 1 and 2 comprises a first radiological examining set of first radiation source means, X-ray tube 23, and a first radiation receptor means, image intensifier 22, having a first common radiation axis A2; and a second radiation examining set of a second radiation source means, X-ray tube 54, and a second radiation receptor means, image intensifier 40, having a second radiation axis A3. The first support means for the first set which includes arms 8 and 9 is rotatable independently of the support means for the second examining set of radiation source and receptor means, X-ray tube 54 and image intensifier 40 and their common radiation axis A3. Further, the second support means for the second radiation means (carrier 43 and wheeled stand 47) are individually movable independently of the first support means (arms 8 and 9), in a direction guided by means including the tracks 46 and 49, either direction being normal to its radiation axis on a path from a position of the radiation means with its axis A3 in alignment with the isocenter, as shown in FIG. 1, to a position remote from the isocenter, leftward on the tracks 46 or 49. In this connection, the isocenter is significant only in that it usually represents the position of the organ of a human patient or other subject under examination, and retracting the radiation means frees access to the subject.

In operation a patient is positioned on the table which is movable in horizontal and vertical planes. Such movement is provided by adjusting the elevation of the table or shifting it from side to side. In this way, the organ to be examined, for example the heart, is located at the isocenter of the system. To conduct the radiological examination of the heart, 50 cc of a radiopaque liquid is injected into a peripheral artery by way of a catheter. The X-ray system is then activited and films or videotape recordings are made of the dynamics of the heart motion. The records are then used for determination of the ventricular volume and valve action. Through the use of the present system, two views of the organ varying in included angle can be made with one injection of radiopaque liquid and the patient need not be titled on the table to obtain the two views.

II—The Embodiment of FIGS. 3 to 6

In FIG. 3 there is shown a radiological examination apparatus 110 comprising a first U-shaped support arm 112 and a second U-shaped support arm 114, pivotally mounted with respect to one another on a common shaft 116, which itself may be rotationally movable in a collar 18 which is fixedly supported on a heavy base 120. The first and second support arms 112 and 114 pivot about a common axis A which is the axis of the common shaft 16. The axis A is in alignment with that portion of a patient P or subject being examined, shown in FIG. 3 on a radiation-transparent table T. The common axis A may be generally horizontally disposed or it may be vertically arranged about the table T and the subject being examined.

The first support arm 112 comprises a pair of hollow generally parallel extended members 122 and 124 connected by a hollow transverse member 126. Each extended member 122 and 124 has a frame 128 at its distal end thereof. On one extended member 122, the frame 128 thereon movable secures a radiation means such as a radiation image receptor 132, and the frame 128 on the other extended member 124 secures a radiation means such as a radiation source 130. The radiation image receptor 130 and the radiation source 130 may move radially with respect to the common axis A, in conjunction with one another to vary the imagery of the radiological examination. The second support arm 114 is arranged in a manner similar to the first support arm 112, except that it has a pair of generally parallel extended members 134 and 136, which may not be as long as the extended members 122 and 124 of the first arm 112 because of their overlapping relationship. The extended members 134 and 136 (only one being shown in FIG. 3 for clarity) are interconnected by a hollow transverse member 138. Each extended member 134 and 136 of the second support arm 114 has a frame 128 at the distal end thereof. On one of the extended members 134, the frame 128 movably secures a radiation means such as a radiation image receptor 130 and the frame 128 on the other extended member 136 movably secures a radiation means such as a radiation source 132 shown more clearly in FIGS. 4 and 5.

Each extended member 122, 124, 134 and 136 is hollow, as is each transverse member 126 and 138, in which hollow space is disposed a system 140 of cables, pulleys and counterweights to facilitate the radially directed movement of the radiation sources 130 and the radiation image receptors 132. A portion of the system 140 is shown in FIG. 6, in one of the extended members 122, wherein a double pulley 142 having two sheaves is disposed in the distal end thereof, near the radiation image receptor 132. Another arrangement of pulleys 144 and 146 is disposed at the elbow or juncture of the interconnecting member 126 and the extended member 122, and a further double pulley 148 having double sheaves is disposed at an intermediate location in the interconnecting member 126. A flexible cable 150 is attached at one end to an arm 152 which slides on rod 156 on the radially outwardly directed side of the frame 128 on the extended member 122. Limit stops 157 are disposed at each end of rod 156. The cable 150 wraps partially around the radially inward portion on one of the sheaves on the double pulley 142 and is carried through the hollow portion of the extended member 122 to wrap around the radially outer side of one of the pulleys 146 at the elbow of the support arm 112, and continues radially inwardly in the transverse member 126 to wrap around a sheave of the further double pulley 148 therein, thence radially outwardly to a weight W of proper balancing characteristics, and continues from the radially outer end thereof around another pulley 144 at the elbow of the support arm 112, out through the extended member 122 and around the other sheave of the double pulley 142 and thence radially inwardly to be secured on an arm 154 on the radially inwardly directed side of the frame 128 on the extended member 122. The frame 128 which comprises a portion of the radiological apparatus is slidable on an end plate 156 on each extended member. An endless cable 158 may be disposed in a figure eight configuration between the second sheave on the double pulley 148 at the intermediate position in the connecting member 120, and a sheave on another double pulley 148' spaced towards the other extended member 124 and which comprises the remaining portion of the funicular system 140 in the first support arm 112. The double pulleys 148 and 148' have their respective sheaves fixedly attached to one another to facilitate selective effectuation of simultaneous radially inwardly and radially outwardly directed movement of the support arms respective radiation image receptor 132 and the radiation source 130. If desired, a single loop can be substituted for the "8" configuration to allow simultaneous movement of the receptor 132 and source 130 in the same direction.

The pulley system in the second support arm 114 is similar to that described in the first support arm 112, wherein the image intensity may be varied according to the particular radial separation of the radiation means. The radiation means on each support arm 112 and 114 are preferably actuated seriatim to eliminate chance of interference between intersecting radiation which might otherwise obfuscate the images of the subject on the film plate. A lock 149 is provided on the bearing member 153 which engages bearing member 116 so as to interlock the support arms 112 and 114 in fixed angular relationship with each other so as to allow the two support arms 112 and 114 to maintain the fixed angular overlapping examination around the common axis A, that is rotational about an isocenter C.

A radiological examination of a patient P is facilitated further by his disposition on a table T, the table itself being movable in any of three directions, two of which are shown by the arrows M in FIG. 5. Of these two directions, one is on a common axis normal to the common axis A and the other allows movement parallel to common axis A. In FIG. 3, the support S for the table T includes an arcuate leg releasable and lockably supported in a base B which is rotatably disposed on a floor stand F. The radiological apparatus comprises radiation sources and radiation receptors which may be moved inwardly and/or outwardly with respect to the common axis A, by manual stipulation or by motorization of the counterweight system, while the support arms 112 and 114 swing around the common axis A, as shown by the arrows R in FIG. 2. Each set of radiation source and receptor has a radiation axis intersecting the rotational axis A at a common isocenter C (FIG. 5) inside the subject of examination. Also the table T rotates about the isocenter normal to the radiation axes and rotational axis A. Rotation of the table and the independent rotation of two U-shaped supports allows examination from all angles inwardly of an imaginary sphere centered on the isocenter C.

III—The Embodiment of FIGS. 7 to 15

In the X-ray apparatus of FIGS. 7 to 15 is shown a large frame 200. Two substantially identical support rings 201A and 201B adjacent each other on a common rotational axis A1 are each rotatably supported by three peripheral rollers 202 at the top of the frame 200 and at 120° therefrom. The rotational axis intersects a radiological examining isocenter C which is usually the position of an organ in the patient P under examination on a table T. Axial movement of each ring is restrained by two sets of conical rollers 203, one conical roller on each side of the bottom of the frame and at 120° therefrom. The two rings are rotated independently of each other by a ring drive motor MX whose shaft 207 is coupled through a gear box 208 to a sprocket shaft 209. At each side of the gear box the sprocket shaft is coupled through electromagnetic clutches CLA and CLB to sprocket wheels 212A and 212B. Sprocket chains 214A and 214B drive the respective rings 201A and 201B.

The ring 201A supports a pair of arms 216A and 217A which extend parallel to the rotational axis A1 near the periphery of the ring. The ring 201A and the two arms 216A and 217A are a first support means for a first radiological examining set consisting of a radiation source, an X-ray tube XA, and a radiation receptor IA. The radiation receptor shown is an image intensifier but may be an X-ray film holder or casette or like means. Both the X-ray tube XA and image receptor IA may be rotated on the arms. As will be described in greater detail, the arms 216A and 217A may be reciprocated from the solid line position shown in FIG. 8 to leftward positions 216A** or 217A* or to corresponding rightward positions 216A* and 217A. In the solid line position, the tube XA and receptor IA are aligned on a common radiation axis A2 through the isocenter C. This alignment is normally maintained by rotation of the radiation set XA and IA during radiological examination so that when the X-ray tube is in the phantom position XA, the image intensifier will be aligned with the tube on axis position A2** although not so shown in FIG. 8. Similarly, when the image intensifier is in position IA*, the X-ray tube will be opposite on the axis position A2* although not so shown.

Figure 8:
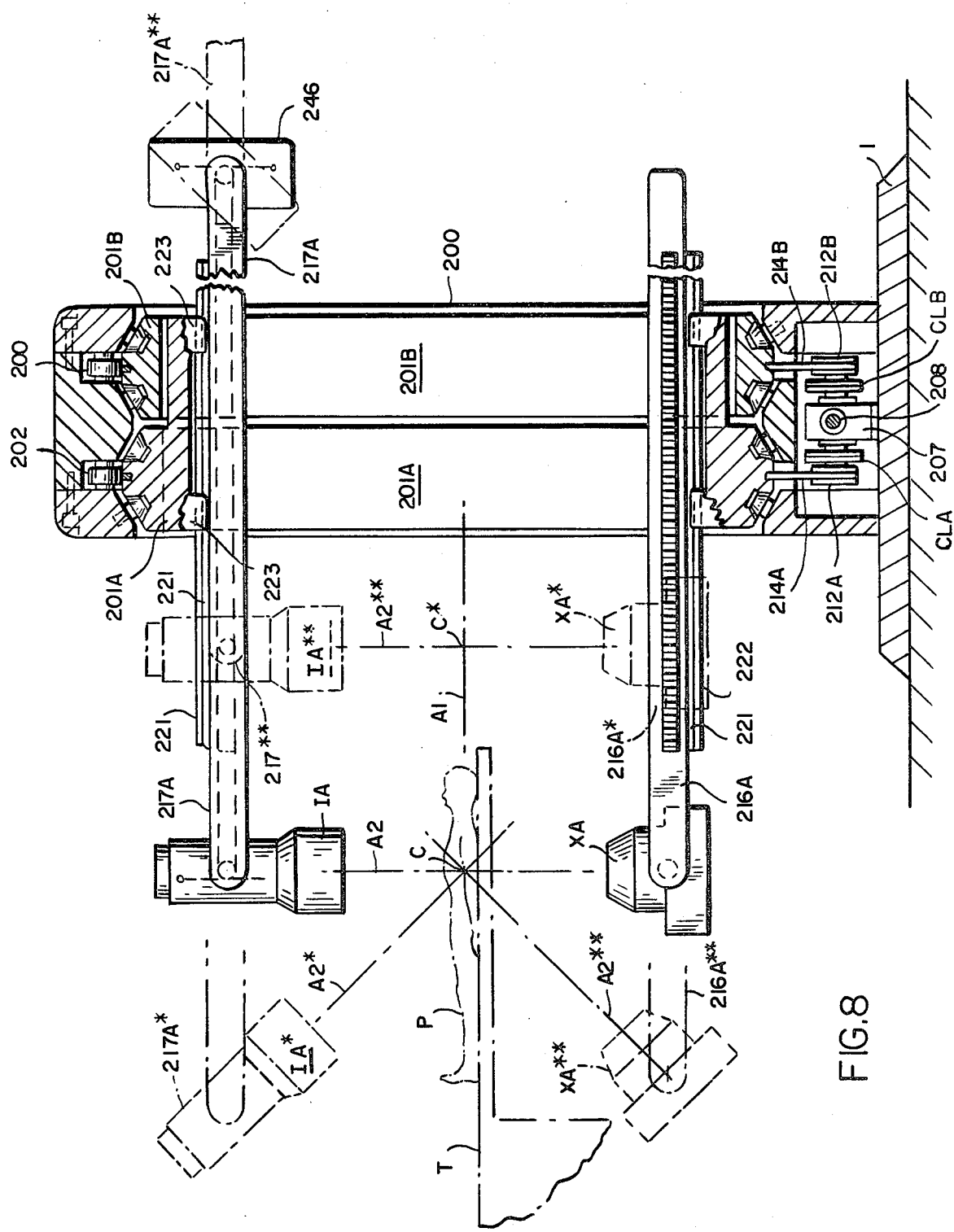
FIG. 8 is a section on line 8—8 of FIG. 7.

What is shown in FIG. 8 is that in addition to being angulated through aligned positions between axes A2* and A1** through the isocenter C, either or both the X-ray tube XA and image intensifier may be independently retracted to parking positions, shown in phantom in FIG. 8 as positions XA* and IA**, in which one or both are remote from the isocenter C and free access of medical personnel to the subject or patient at the isocenter.

The retraction or parking of one or both radiation source and receptor means in an examining set is particularly critical when, as in the present invention, there are two radiological examining sets. In the embodiment of FIGS. 7 to 15, the second support ring 201B has a pair of reciprocating arms 216B and 217B respectively supporting a second radiological examining set consisting of a second X-ray source XB and a second image receptor IB. This second set is normally aligned on a second radiation axis A3 intersecting the isocenter C. The second set can be angulated and retracted in the same way as described for the first set and independently thereof, and further can be rotated on the second ring 201B independently of the first set so that the plane of its examination of a subject at the isocenter, that is the examining angle of the second radiation axis may be selected independently of the examining angle of the first axis, and the included angle between the two axes may be varied throughout nearly 180°, the range of relative rotation of the two support rings, which, however, can rotate coordinately through 360°.

Figure 14:
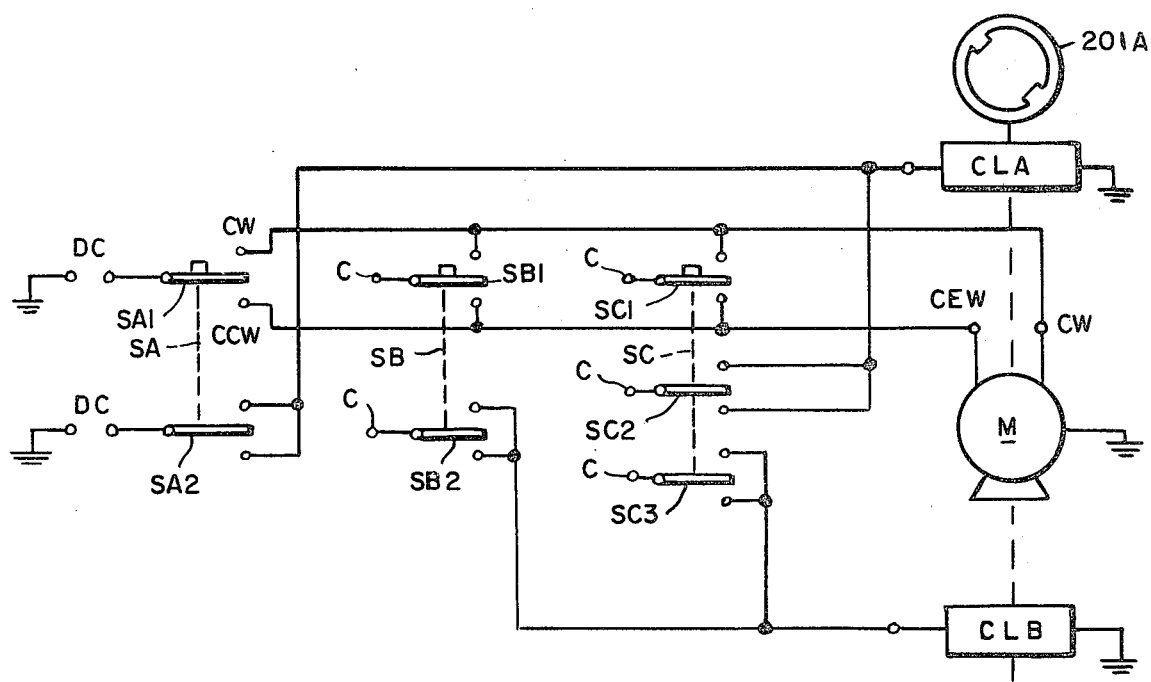
FIGS. 14 and 15 are electrical diagrams of the circuits controlling the motors driving the apparatus of FIG. 7.

FIG. 14 shows the electrical control circuit by which the two rings 201A and 201B are rotated by the motor M. A first push button manual switch SA has a first contactor SA1 which applies power from a source DC to either of two contacts CW or CCW connected to corresponding terminals on the motor M to turn it clockwise or counterclockwise. The power source may be direct or single phase alternating current but is preferably three phase for a servo or stepping motor M. A second contactor SA2, ganged to the first contactor SA1, in either of its positions energizes and closes the electromagnetic cluth CLA coupled to the first ring 201A, selecting that ring for rotation in the direction chosen by the position of the first contactor SA1. Similarly, the contactors SB1 and SB2 of a second ganged push button switch SB choose the drive of the second ring 201B. Both rings may be rotated coordinately by use of a third, triple ganged pushbutton switch SC whose first contactor SC1 selects the direction of rotation as does the first switch contactor SA1. The two directional contactors SC2 and SC3 energize and close the clutches CLA and CLB to both rings, driving the rings in the same direction.

Figure 15:
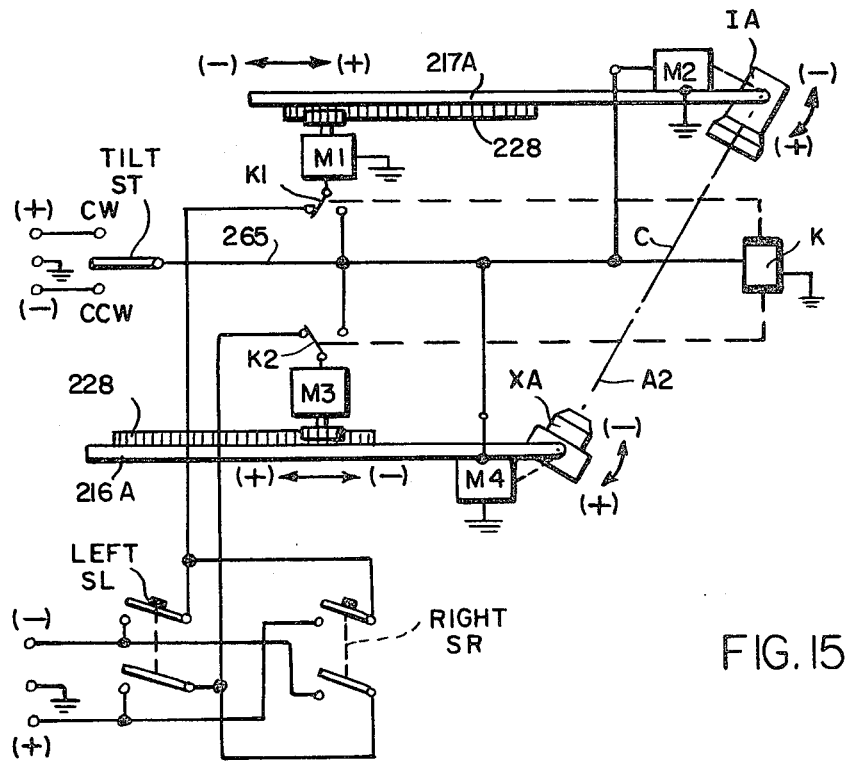

Each of the four reciprocal arms 216A, 217A, 216B and 217B on the rings 201A and 201B comprises a hollow rectangular beam, one such beam arm 217A being shown in section in FIG. 10. On the outer side of the beam, a rail 221 extends to a rod 222 extending the length of the reciprocal traverse of the arm. The rod 222 slides in two linear bearings 223 carried on a step 224, each ring having two steps. On the steps for arms 216A, 217A, 216B and 217B respectively are four reciprocal drive motors of which one motor M1 is shown in FIG. 11. Like motors M1 and M3 are shown in FIG. 15. As shown in FIG. 11, the motor M1 for reciprocating the first image receptor arm 216A is connected through a gear box 226 to a pinion gear 227 meshed in a rack extending the length of the reciprocal traverse of the arm 216A. Similarly, drive motor M3 and two others are connected to racks on the other three drives.

In addition to the reciprocal drive of their supporting arms, the two X-ray tubes XA and XB and image intensifiers IA and IB are titled on their respective supporting arms, usually in coordination such that, as previously explained, the radiation source and receptor of each radiological set on one ring are kept precisely aligned on one of the radiation axes A2 or A3 (FIGS. 1 and 15). The four radiation source and receptor means are titled by motors of which one motor M2 tilting the first image intensifier IA on arm 216A of ring 201A is shown in FIGS. 9 and 10, and a motor M4 tilting the corresponding X-ray tube XA of the same first radiological set is shown in FIG. 15. The tilting motors for the second radiological set of source XB and receptor IB on ring 201B are arranged and operate in the same way.

Figure 13:
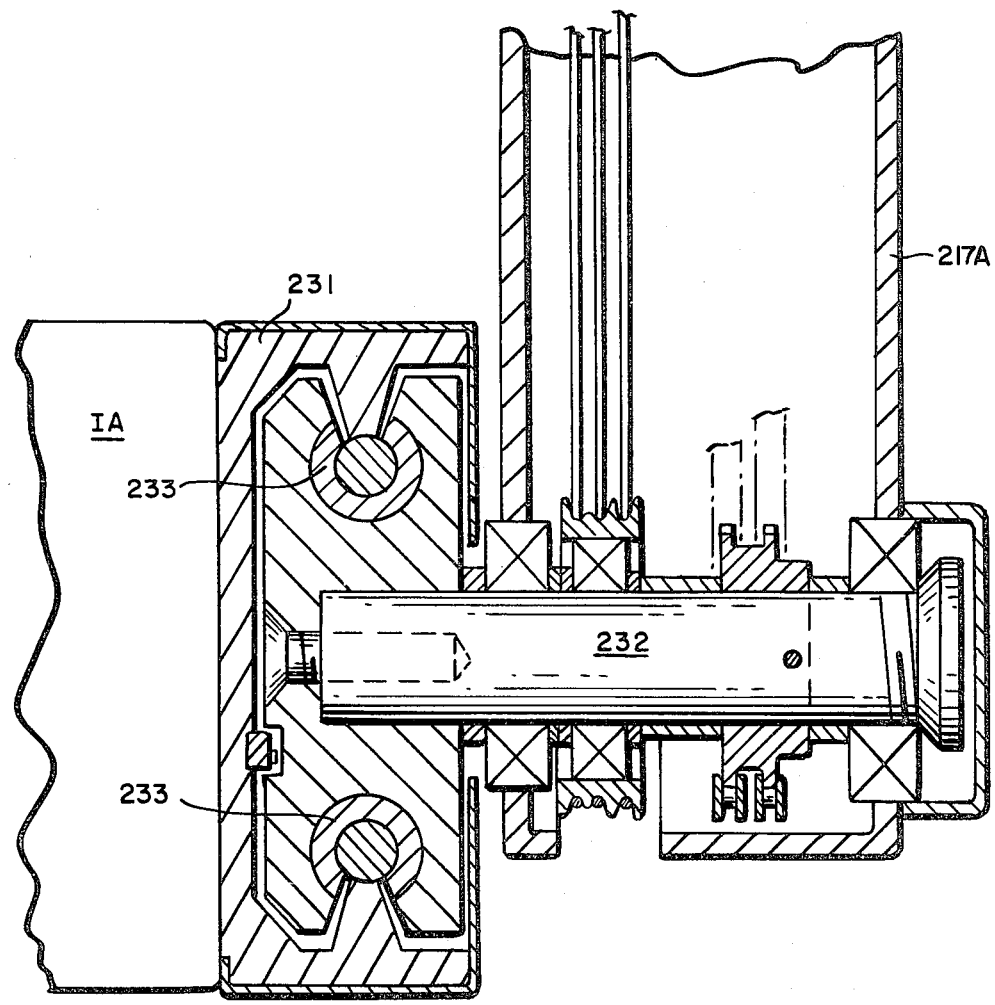
FIG. 13 is a section on line 13—13 of FIG. 10.

As shown in FIGS. 9, 10 and 13, the first image intensifier IA is attached to a carriage 231 which rotates on a tilt shaft 232 journalled on arm 216A and which axially reciprocates on linear bearings 233 carried on the tilt shaft in a known manner (FIG. 13). The tilt shaft 232 is driven by the image intensifier tilt motor M2 through a gear box 234 (FIG. 9). The gear box in turn drives first and second ellipsoidal gears 236 and 237. The second ellipsoidal gear 237 turns with the same axle 238 as a first spur gear 239 meshed with a second spur gear 241 keyed on the tilt shaft 232 for the image intensifier carriage 231. Thus, rotation of the motor M2 tilts the image intensifier IA in clockwise or counterclockwise direction.

Since it is difficult or impossible to locate the image intensifier tilt shaft 232 exactly on an axis through the image intensifier center of gravity, a rotating counterweight 246 has a pivot 245 at the other end of the first image intensifier arm 217A (FIGS. 8 and 12). Tilting and reciprocation of the image intensifier IA and its carriage 231 are transmitted to the counterweight 246 through a tilt pulley 247 keyed to the tilt shaft 232 and a reciprocation pulley 248 rotatively journalled on the tilt shaft by bearings 249. A tilt cable 251 around the tilt pulley 247 and a corresponding pulley 252 on the counterweight pivot 245 causes the counterweight 246 to tilt in compensation for the shift of the image intensifier IA center of gravity with respect to the axis of rotation A1 of its supporting ring 201 A. Two cables 253 and 254 are connected around the reciprocation pulley 248 journalled on the image intensifier tilt shaft and a corresponding pulley 256 on the counterweight pivot 245. The ends of the two cables are anchored at one end on upper and lower brackets 257 and 258 on the image intensifier carriage 231, and at the other end on corresponding brackets 261 and 262 supporting the counterweight 246 on the arm 217A. Similar corresponding reciprocal and tilting drive motors and counterweighting systems are provided for the X-ray tube XA on the other arm 216A of the first ring 201A and for the second X-ray tube XB and image itensifier IB on the second ring 201B.

FIG. 15 illustrates the electrical control circuit for the reciprocal drive of the first set of arms 216A and 217A and the tilting of the first radiological set of X-ray source XA and image receptor IA carried on the respective arms. The reciprocation of the X-ray source arm 216A to the left is denoted by a plus sign (+) and to the right by a minus sign (−) as indicated by one double headed arrow. The signs are reversed for the upper arm 217A. As in FIG. 14, a simplified (+) (−) direct current power supply is shown, although two or three phase alternating current supplies are preferred and can be routinely adapted to the circuit shown.

The control circuit of FIG. 15 includes a tilt switch ST which selects the direction of rotation of the radiation means of a set XA-IA and a pair of switches SR and SL respectively for reciprocation of the arms 216A and 217A jointly to the right or left. During examination of a subject on the radiation axis A2, the tilt or angulation switch ST only will be used to tilt the radiation source XA and receptor IA and simultaneously reciprocate one arm left or right and the other arm oppositely so that the radiation axis pivots about the isocenter C. Turning the tilt switch ST to the CW position, for example, connects the plus power supply terminal (+) to a bus 265 leading to a relay coil K which, regardless of its applied voltage polarity is energized and transfers its contacts K1 and K2 from the position shown in FIG. 15 to a position connecting the bus 265 to the reciprocal motors M1 and M3. The corresponding arms 216A and 217A respectively will be driven left and right. Concomitantly, the tilt motors M2 and M4 will receive a positive voltage which will tilt both the source XA, receptor IA and their axis AZ clockwise (CW). Thus the four motors M1, M2, M3 and M4 can reciprocally drive the arms 216A and 217A and rotatively tilt the radiation means thereon, independently or interdependently. Stepping or servo motors are used to insure that the reciprocation and tilting is precisely coordinated to maintain alignment of the common radiation axis of the radiation source XA and the receptor IA.

Because the first radiological examining set XA-IA is only one of the two sets around the subject or patient, it may be necessary to free the access to the patient by retraction of the first or both sets from the isocenter C. First the tilt switch ST angulates the radiation set to a vertical position as shown by the positions IA and XA in FIG. 8. Release of the tilt switch ST then returns it to the position shown in FIG. 15, deenergizing relay K and releasing its contacts K1 and K2 to the positions shown. Then closing the LEFT switch SL, for example, will apply appropriately polarized power to the reciprocal motors M1 and M3 only causing them to retract or park the arms 216A and 217A and their radiation set to the left positions XA* and IA** shown in FIG. 8. To return the set to the position XA and IA a RIGHT switch SR is closed driving the motors M1 and M3 in the opposite direction. An identical circuit controls reciprocation of the support arms 216B and 217B on the second ring 201B and tilting of the second radiological set of X-ray source XB and receptor IB on those arms.

In addition to allowing parking of one or both radiological sets, the apparatus of FIGS. 7 to 15 and that of FIGS. 1 and 2 permit movement of the radiation axis of one set out of coincidence at the common isocenter C with the other set but still aligned with the same subject. By way of illustration in FIG. 8, the intersection of the radiation axis of the parked radiation set IA**-XA* with the rotational axis A1 at C* is displaced from the previously common isocenter C on the radiation axis of the other radiation set IB-XB. In practice the isocenter C* of the first set would not be at parked position but rather closer, typically about six inches or less, to the isocenter C of the other set. This relative movement of the isocenters of the two radiation sets permits somewhat different views of an organ in the subject under examination.

While specific embodiments of the invention have been shown and described for illustration, it should be understood that the scope of the invention is defined in the claims following.

I claim:
1. Radiological apparatus for radiographic examination of a subject comprising:
 a first radiological examining set including first radiation source means, first radiation receptor and two-dimensional image-former means and first support means for holding the first source and receptor means on a first radiation axis; and
 a second radiological examining set including second radiation source means, second radiation receptor and two-dimensional image-former means and second support means for holding the second source and receptor means on a second radiation axis aligned to intersect the first radiation axis at a common isocenter, wherein the first support means is rotatable independently of the second support means about a rotational axis intersecting the common isocenter;

whereby a series of substantially simultaneous radiographic examinations can be made on both radiation axes through the subject at variable angles between the radiation axes.

2. Apparatus according to claim 1 wherein one radiological set is movable through spherical loci concentric with the isocenter.

3. Apparatus according to claim 1 wherein both radiological sets are movable through spherical loci concentric with the isocenter.

4. Apparatus according to claim 1 wherein both support means are rotatable independently of each other.

5. Apparatus according to claim 1, 2, 3 or 4 wherein the radiation means on one support means are tiltable on their support means.

6. Apparatus according to claim 1, 2, 3 or 4 wherein the radiation means on both support means are tiltable on their supports.

7. Apparatus according to claim 1 wherein both support means are rotatable on a common axis.

8. Apparatus according to claim 1 in combination with a table for supporting a subject, the table being tiltable to rotate the subject about the isocenter and a point within the subject.

9. Apparatus according to claim 1 wherein the support means for one radiation means in one set is movable independently of the support means for the other radiation means in the same set.

10. Apparatus according to claim 9 wherein the movement is on a reciprocal path.

11. Apparatus according to claim 9 wherein the movement is reciprocal to a position remote from the isocenter freeing access to a subject at the isocenter.

12. Apparatus according to claim 11 wherein the reciprocation is parallel to the rotational axis of the radiation means.

13. Apparatus according to claim 1 wherein the support means for one radiation means in a set is movable independently of the support means for the other radiation means of the same set and includes means guiding the independent movement of the support means on a path from a position of the radiation means in alignment with the common isocenter to a position displaced from the common isocenter.

14. Apparatus according to claim 9 wherein the support means for both radiation means of a set are reciprocally and independently movable in the same direction.

15. Apparatus according to claim 14 including a room with ceiling and floor portions and tracks for guiding reciprocation of respective radiation means in a set on those positions.

16. Apparatus according to claim 14 wherein the tracks include stops for aligning the radiation axis of the respective radiation means with the common isocenter.

17. Apparatus according to claim 15 wherein the radiation axis is aligned at an angle to the tracks.

18. Apparatus according to claim 9 wherein the support means for one radiation set comprises two arms respectively carrying a radiation source and receptor means, and means reciprocally supporting respective arms.

19. Apparatus according to claim 18 including motor means for reciprocally driving the two arms for one radiation set independently of each other.

20. Apparatus according to claim 9 including motor means for driving the two arms for one radiation set independently or interdependently reciprocally.

21. Apparatus according to claim 1 or 9 wherein the support means for the first radiation set includes a frame and a ring rotatable therein on the rotational axis.

22. Apparatus according to claim 21 wherein the support means for the second set includes a ring rotatable on the same rotational axis and frame.

23. Apparatus according to claim 22 including means for driving the rings and their respective radiation sets independently.

* * * * *